United States Patent
Lindell et al.

(10) Patent No.: US 9,353,022 B2
(45) Date of Patent: May 31, 2016

(54) PROCESS FOR CONVERSION OF NATURAL GAS TO HYDROCARBON PRODUCTS AND A PLANT FOR CARRYING OUT THE PROCESS

(71) Applicant: Haldor Topsøe A/S, Kgs. Lyngby (DK)

(72) Inventors: Kristian Lindell, Kävlinge (DK); Thomas Sandahl Christensen, Lyngby (DK); Michael Hultqvist, Lyngby (DK); Kim Aasberg-Petersen, Allerød (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 14/556,342

(22) Filed: Dec. 1, 2014

(65) Prior Publication Data

US 2015/0152019 A1 Jun. 4, 2015

Related U.S. Application Data

(60) Provisional application No. 61/910,664, filed on Dec. 2, 2013.

(30) Foreign Application Priority Data

Dec. 2, 2013 (DK) ................................ 2013 70736

(51) Int. Cl.
*C07C 1/04* (2006.01)
*B01J 8/06* (2006.01)
(Continued)

(52) U.S. Cl.
CPC . *C07C 1/041* (2013.01); *B01J 8/02* (2013.01); *B01J 8/065* (2013.01); *B01J 8/08* (2013.01);
(Continued)

(58) Field of Classification Search
CPC ........ B01J 2208/027; B01J 8/02; B01J 8/065; B01J 8/08; C01B 2203/0233; C01B 2203/0244; C01B 2203/0261; C01B 2203/0475; C01B 2203/062; C01B 3/38; C01B 3/382; C07C 1/041
USPC .......................................... 422/187; 518/702
See application file for complete search history.

(56) References Cited

U.S. PATENT DOCUMENTS 5,621,155 A * 4/1997 Benham et al. ............... 585/310
6,114,400 A 9/2000 Nataraj et al.
(Continued)

FOREIGN PATENT DOCUMENTS

EP 0 516 441 A1 12/1992
EP 2 253 585 A1 11/2010
(Continued)

OTHER PUBLICATIONS

Aasberg-Petersen ("Natural gas to synthesis gas—Catalysts and catalytic processes" Journal of Natural Gas Scien and Engineering 3 (2011) 423-459).*

*Primary Examiner* — Jafar Parsa
*Assistant Examiner* — Amy C Bonaparte
(74) *Attorney, Agent, or Firm* — Blank Rome LLP

(57) ABSTRACT

A process for the conversion of natural gas to hydrocarbon products by (a) mixing natural gas with a small amount of hydrogen, (b) purifying the mixture from (a) to obtain purified natural gas, (c) mixing the purified natural gas from (b) with steam to obtain the desired steam-to-carbon (S/C) ratio, (d) mixing the natural gas/steam mixture from (c) with tail gas from the downstream Fischer-Tropsch synthesis and converting the mixture into a synthesis gas, (e) cooling the synthesis gas from (d) and condensing out the process water from it, (f) leading the dry synthesis gas from (e) to a carbon dioxide removal section, and (g) sending the CO2-deprived synthesis gas to the downstream Fischer-Tropsch synthesis unit as a make-up gas. The carbon dioxide removed from the syngas in step (f) is either vented or kept for other use without any part of it being recycled.

10 Claims, 1 Drawing Sheet

(51) Int. Cl.
*B01J 8/02* (2006.01)
*B01J 8/08* (2006.01)
*C01B 3/38* (2006.01)

(52) U.S. Cl.
CPC . *C01B 3/38* (2013.01); *C01B 3/382* (2013.01); *B01J 2208/027* (2013.01); *C01B 2203/0233* (2013.01); *C01B 2203/0244* (2013.01); *C01B 2203/0261* (2013.01); *C01B 2203/0475* (2013.01); *C01B 2203/062* (2013.01)

(56) References Cited

U.S. PATENT DOCUMENTS

| | | | |
|---|---|---|---|
| 6,375,916 | B2 | 4/2002 | Christensen et al. |
| 6,495,610 | B1 * | 12/2002 | Brown .................. 518/706 |
| 2005/0209347 | A1 | 9/2005 | Bowe |
| 2013/0065974 | A1 | 3/2013 | Kresnyak |

FOREIGN PATENT DOCUMENTS

| WO | WO 00/09441 A2 | 2/2000 |
|---|---|---|
| WO | WO 01/60773 A1 | 8/2001 |

\* cited by examiner

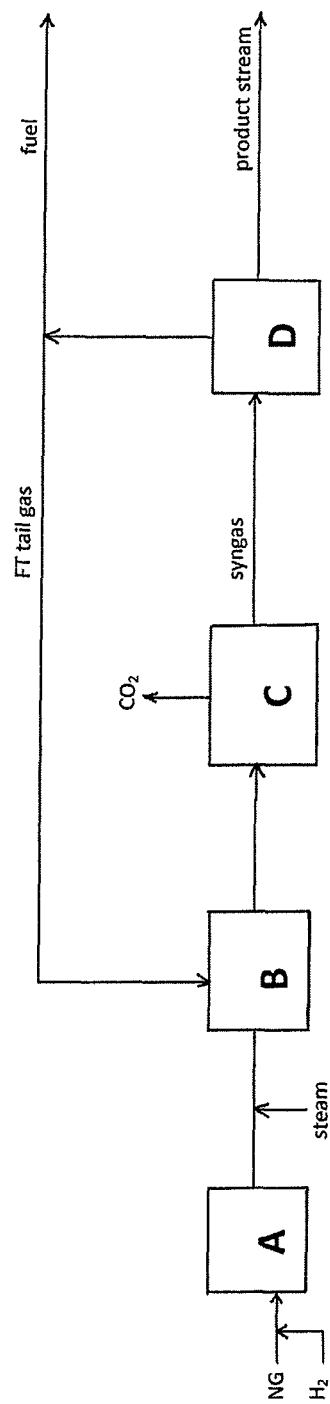

PROCESS FOR CONVERSION OF NATURAL GAS TO HYDROCARBON PRODUCTS AND A PLANT FOR CARRYING OUT THE PROCESS

BACKGROUND OF THE INVENTION

1. Field of the Invention

The present invention relates to a process for conversion of natural gas to hydrocarbon products. More specifically, the invention relates to a Fischer-Tropsch synthesis process characterized by including a Fischer-Tropsch tail gas recycle and a carbon dioxide removal, but no carbon dioxide recycle. The invention further relates to a plant for carrying out the process.

2. Description of the Related Art

Steam reforming processes produce synthesis gas (syngas) with a ratio module $H_2/CO$ between 2 and 5. By reducing the steam-to-carbon ratio (S/C ratio), the $H_2/CO$ ratio can be lowered. Addition of carbon dioxide ($CO_2$) or recycling of $CO_2$ can also be used to reduce the S/C ratio in syngas manufacturing.

The Fischer-Tropsch (FT) process involves a series of chemical reactions that produce a variety of hydrocarbons, ideally with the formula $C_nH_{(2n+2)}$. The more useful reactions produce alkanes as follows:

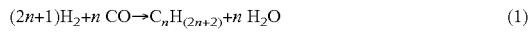

$$(2n+1)H_2 + n\,CO \rightarrow C_nH_{(2n+2)} + n\,H_2O \qquad (1)$$

where n is typically 10-20. The formation of methane (n=1) is unwanted. Most of the alkanes produced tend to be straight-chain, suitable as diesel fuel. In addition to alkane formation, competing reactions give small amounts of alkenes, as well as alcohols and other oxygenated hydrocarbons.

The FT process is a key component of gas-to-liquids (GTL) technology, and it can produce synthetic lubrication oils and synthetic fuels, typically from natural gas, coal or biomass.

For GTL plants based on FT synthesis, the required $H_2/CO$ ratio typically is approximately 2.0. This is normally obtained by operating within low S/C ratios and by recycling a small part of the excess tail gas from the FT synthesis. If too much FT tail gas is recycled, then the $H_2/CO$ ratio will become too low. For FT synthesis based on cobalt catalyst systems, the reactants are $H_2$ and CO, while $N_2$, $CO_2$ and $CH_4$ all are inert in the synthesis. Too high amounts of these inert compounds entail the disadvantage that the conversion to hydrocarbons in the FT section is reduced. The FT tail gas contains the inert components from the FT synthesis ($CO_2$ and $N_2$) and unconverted $H_2$ and CO together with light hydrocarbons formed in the FT synthesis. Therefore a recycling of FT tail gas acts to adjust the syngas module through the presence of $CO_2$, but also to recycle the unconverted hydrocarbons.

The present invention is based on combining the removal of $CO_2$ from the produced syngas with a recycling of FT tail gas. Normally those skilled in the art would only use one of these techniques to obtain the target $H_2/CO$ ratio. The removal of $CO_2$ can be carried out by several techniques, including $CO_2$ wash systems or $CO_2$ selective membranes. Such systems are used in syngas plants for ammonia or in CO plants for the final clean-up of the syngas. However, the $CO_2$ removal section is normally regarded as an extra capital investment, and it is not used in GTL plants based on FT synthesis.

The prior art within the field of the present invention distinguishes between (1) FT tail gas recycle but no $CO_2$ removal or recycle and (2) FT tail gas recycle and $CO_2$ removal and recycle. These two scenarios can be described as follows:

(1) FT Tail Gas Recycle but no $CO_2$ Removal or Recycle

Natural gas is mixed with a small amount of hydrogen, compressed (if required) and heated to the required temperature before entering the feed purification section, which consists of one or several catalytic reactors. In said section, impurities such as (but not limited to) sulfur, chlorine and heavy metals are removed from the natural gas. The natural gas is then mixed with steam, whereby the desired S/C ratio is obtained. The mixture of natural gas and steam is then (after a pre-heating, if this is decided beneficial) mixed with an off-gas coming from the downstream FT synthesis process, the so-called FT tail gas. This mixture of natural gas, steam and FT tail gas is converted into a synthesis gas, mainly consisting of hydrogen, carbon monoxide, carbon dioxide and a small amount of residual methane, in the reforming section. The mixing ratio between natural gas and FT tail gas can be used to control the ratio between hydrogen and carbon monoxide in the produced synthesis gas. The reforming section can consist of one or several catalytic reactors and/or reformers, for example an adiabatic pre-reformer, a tubular reformer and/or an autothermal reformer (ATR) consisting of a burner for partial oxidation of the feed stream with oxygen and an adiabatic catalyst bed. The synthesis gas leaving the reforming section is cooled in a waste heat boiler and boiler feed water pre-heaters before being further treated in additional catalytic reactors, if required, for example for final adjustment of product gas composition, or removal of impurities. The synthesis gas is then cooled further, and the excess process water is condensed and removed. The almost dry synthesis gas is then sent to the downstream Fischer-Tropsch synthesis process as make-up gas.

(2) FT Tail Bas Recycle and $CO_2$ Removal and Recycle

Natural gas is mixed with a small amount of hydrogen, compressed (if required) and heated to the required temperature before entering the feed purification section, consisting of one or several catalytic reactors. In the feed purification section, impurities such as (but not limited to) sulfur, chlorine and heavy metals, are removed from the natural gas. The purified natural gas is then mixed with steam, whereby the desired S/C ratio is obtained. The mixture of natural gas and steam is then (after pre-heating if this is decided to be beneficial) mixed with an off-gas coming from the downstream FT synthesis process, the so-called FT tail gas, and $CO_2$ is recycled from the downstream $CO_2$ removal process. This mixture of natural gas, steam, $CO_2$ and FT tail gas is converted into a synthesis gas, mainly consisting of hydrogen, carbon monoxide, carbon dioxide and a small amount of residual methane, in the reforming section. The mixing ratio between natural gas, $CO_2$ and the FT tail gas can be used to control the ratio between hydrogen and carbon monoxide in the produced synthesis gas. The reforming section can consist of one or several catalytic reactors and/or reformers, for example an adiabatic pre-reformer, a tubular reformer and/or an autothermal reformer (ATR) consisting of a burner for partial oxidation of the feed stream with oxygen and an adiabatic catalyst bed. The synthesis gas leaving the reforming section is cooled in a waste heat boiler and boiler feed water pre-heaters before being further treated in additional catalytic reactors, if required, for example for final adjustment of the product gas composition or for removal of impurities. The synthesis gas is then cooled further, and the excess process water is condensed and removed. The almost dry synthesis gas is then sent to the $CO_2$ removal unit, where a larger or smaller part of the $CO_2$ is removed from the synthesis gas. The synthesis gas, now containing less $CO_2$, is sent to the downstream FT synthesis process as make-up gas, and after compression in the $CO_2$ recycle compressor, the $CO_2$-rich stream is recycled, either fully or partly, to the reforming section. In case the $CO_2$ is only partly recycled, the excess $CO_2$ kept for other use, either before or after compression.

From U.S. Pat. No. 6,375,916 B2 it is known to treat a hydrocarbon feed containing higher hydrocarbons by first pre-reforming the feed to remove or reduce the content of higher hydrocarbons and then passing the effluent from the pre-reformer to an ATR. The process is preferably operated at low S/C ratios, since a low S/C ratio lowers the investment expenses for an ATR plant and reduces the energy consumption in operating the plant. However, this patent is silent about any tail gas recycle and also about removal of $CO_2$ from ATR syngas.

EP 0 516 441 A1 describes a process for the conversion of natural gas into higher hydrocarbons. The natural gas is reacted with steam in a reformer to produce a first product stream containing CO, $CO_2$ and $H_2$, which is then passed to a Fischer-Tropsch reactor without separation of $CO_2$, whereby a second product stream including hydrocarbons and $CO_2$ is produced. This second product stream is passed to a product recovery unit, where the desired hydrocarbon products are recovered, leaving a third product stream containing $CO_2$. At least a portion of this third product stream is recycled to the reformer. The EP application does not mention or envisage the possibility of removing all $CO_2$ from the syngas and avoiding any recycling thereof.

US 2013/0065974 A1 discloses a process for synthesizing hydrocarbons, said process more specifically being an enhanced FT process for the synthesis of sulfur-free, clean burning hydrocarbon fuels, examples of which include synthetic diesel and aviation fuel. In the process, naphtha is a mandatory part of the hydrocarbons produced, and at least a portion of said naphtha is recycled to the syngas generator to obtain an enhanced hydrogen-rich stream and thereby enhance the synthesis of hydrocarbons. The process according to the present invention distinguishes itself from the process of the US application in that no naphtha recycle is involved. The process of the US application does include a $CO_2$ removal step, which is however optional, and if any $CO_2$ is removed, at least part of it is re-introduced into the ATR via the pre-treatment unit to enhance the production of synthetic diesel.

It is well-known to produce a synthesis gas by either ATR or SMR (steam methane reforming) followed by subsequent removal of part of the $CO_2$.

The above in combination with recycling a part of or all of the removed $CO_2$ to the inlet of the reformer is also known. This includes adjusting the $H_2/CO$ ratio for the subsequent FT synthesis section to the desired value around 2.

Furthermore it is known to produce liquid fuels from syngas by fluid bed Fischer-Tropsch synthesis. A typical plant produces syngas in one or more reformer trains, each consisting of a desulfurizer, a top fired primary (steam) reformer and a secondary (oxygen-fired autothermal) reformer. Part of the natural gas is bypassed around the primary reformer and fed to the secondary reformer together with recycled tail gas. To adjust the $CO_2$ concentration to the desired level (around 6.5%) for entering the FT synthesis unit, part of the exit stream from the secondary reformer is subjected to $CO_2$ removal without recycling. The $CO_2$ thus removed is exported for recovery as a liquid stream. Thus it is known to remove $CO_2$ without recycling, but the feed stream to the FT synthesis unit still contains a certain amount of $CO_2$ because a part of the $CO_2$-containing stream from the reformer bypasses the $CO_2$ removal step.

Various processes for the conversion of hydrocarbon-containing gases, especially natural gas, to hydrocarbon products are known in the art. Thus, as already mentioned, it is known to convert natural gas to syngas by reaction with steam and optionally oxygen. If the feed contains significant amounts of higher hydrocarbons ($C_{2+}$), pre-reforming can be used to convert these higher hydrocarbons into syngas according to the reactions:

$$C_nH_m + n\,H_2O \rightarrow nCO + (n+m/2)H_2 \quad (2)$$

$$3\,H_2 + CO \leftrightarrow CH_4 + H_2O \quad (3)$$

$$CO + H_2O \leftrightarrow CO_2 + H_2 \quad (4)$$

The syngas thus obtained can then be converted to desired hydrocarbon products by using the FT process.

Autothermal reforming (ATR) is a technology commonly used for the production of syngas, where the conversion of a hydrocarbon feedstock, such as natural gas, is carried out in a single reactor through the combination of partial combustion and adiabatic steam reforming. The ATR reactor consists of a burner, a combustion chamber and a fixed bed catalyst section contained in a refractory lined pressure shell. The key elements in the ATR reactor are the burner and the catalyst bed. Combustion of the hydrocarbon feed is carried out with sub-stoichiometric amounts of air, enriched air or oxygen by flame reactions in a burner combustion zone. The burner provides mixing of the feed streams, and the natural gas is converted in a turbulent diffusion flame, often simplified by the reaction $$CH_4 + 3/2\,O_2 \rightarrow CO + 2\,H_2O \quad (5)$$

The catalyst bed equilibrates the methane steam reforming reaction (the reverse of reaction (3) above) and the shift reaction (reaction (4) above).

When natural gas, typically a mixture of predominantly methane with some higher hydrocarbons, nitrogen and $CO_2$, is used as the only carbon-containing material in the feed to the reformer, the syngas obtained is not optimal for use in the FT reaction because of the $H_2/CO$ ratio. Therefore it is normal practice to remove the $CO_2$, which is co-produced during the reforming process, and recycle the desired quantity back to the reforming section. The addition of this $CO_2$ to the feed changes the $H_2/CO$ ratio. Careful control of the amount of recycled $CO_2$ allows a desirable $H_2/CO$ ratio to be achieved.

SUMMARY OF THE INVENTION

It has now surprisingly been found that it is possible to refrain from recycling any $CO_2$ to the reforming section after removing it from the syngas and simultaneously use part of the tail gas from the FT synthesis unit. This way the efficiency of the plant can even be increased.

Thus, the present invention relates to a process for the conversion of natural gas to hydrocarbon products, said process comprising the steps of:
  (a) mixing natural gas with a small amount of hydrogen,
  (b) purifying the mixture from (a) in a feed purification section to obtain purified natural gas,
  (c) mixing the purified natural gas from (b) with steam to obtain the desired steam-to-carbon (S/C) ratio,
  (d) mixing the natural gas/steam mixture from (c) with the tail gas from the downstream Fischer-Tropsch (FT) synthesis or a part thereof in a syngas section and converting the mixture into a synthesis gas,
  (e) cooling the synthesis gas from (d) and condensing out the process water from it,
  (f) leading the dry synthesis gas from (e) to a carbon dioxide removal unit, where the $CO_2$ is removed from the synthesis gas, and (g) sending the CO$_2$-deprived synthesis gas to the downstream Fischer-Tropsch synthesis unit as a make-up gas, wherein the carbon dioxide removed from the syngas in step (f) is either vented or kept for other use.

If only a part of the tail gas from the FT synthesis unit is recycled, then the non-recycled part of the tail gas is preferably used as a fuel.

The syngas section preferably comprises one or several catalytic reactors and/or reformers such as an adiabatic pre-reformer, a tubular reformer, a catalytic partial oxidation (CPO) reformer and/or an autothermal reformer (ATR) consisting of a burner for partial oxidation of the feed stream with oxygen and an adiabatic catalyst bed. The syngas section may also include a heat exchange reformer, either in parallel with the SMR and/or ATR or upsteam and in series with the SMR and ATR. It is preferred that the syngas section comprises a steam methane reformer (SMR), an autothermal reformer (ATR), a catalytic partial oxidation (CPO) reformer or a combination of these reforming technologies. In another embodiment, it is preferred that the syngas section comprises a pre-reformer combined with an autothermal reformer (ATR).

The FT tail gas is preferably added directly to the SMR, ATR or CPO reformer. In another preferred embodiment, the FT tail gas is added to the desulfurization reactors or to the adiabatic pre-reformer.

The temperature in the FT synthesis unit is preferably in the range of from 150 to 350° C., especially 180 to 240° C., and the pressure is in the range of from 100 to 10.000 kPa (0 to 100 barg), especially 1000 to 5000 kPa (10 to 50 barg). The catalyst in the FT synthesis unit is preferably based on a transition metal selected from cobalt, iron and ruthenium.

BRIEF DESCRIPTION OF THE DRAWING

FIG. 1 shows the plant for carrying out the process for the conversion of natural gas to hydrogen products of the present invention.

DETAILED DESCRIPTION OF THE PREFERRED EMBODIMENTS

The process according to the invention can be described as follows, referring to the attached FIG. 1:

Natural gas is mixed with a small amount of hydrogen, compressed if required, and heated to the required temperature before entering the feed purification section A. In the feed purification section, consisting of one or several catalytic reactors, impurities such as (but not limited to) sulfur, chlorine and heavy metals are removed from the natural gas. The purified natural gas is then mixed with steam to obtain the desired S/C ratio. The natural gas/steam mixture is (after pre-heating, if this is decided to be beneficial) mixed with an off-gas coming from the downstream FT synthesis process, the so-called FT tail gas. This mixture of natural gas, steam and FT tail gas is converted into a synthesis gas, mainly consisting of hydrogen, carbon monoxide, carbon dioxide and a small amount of residual methane, in the syngas section B. The mixing ratio between natural gas and the FT tail gas can be used to control the ratio between hydrogen and carbon monoxide in the produced synthesis gas—this ratio is typically around 2. The syngas section B can consist of one or several catalytic reactors and/or reformers, for example an adiabatic pre-reformer, a tubular reformer, a catalytic partial oxidation (CPO) reactor and/or an autothermal reformer (ATR), which consists of a burner for partial oxidation of the feed stream with oxygen and an adiabatic catalyst bed. Other possibilities include a heat exchange reformer, either in parallel with the SMR and/or ATR or upsteam and in series with the SMR and ATR. The syngas leaving the syngas section is cooled in a waste heat boiler and boiler feed water pre-heaters before being further treated in additional catalytic reactors, if required, for example for final adjustment of the product gas composition or for removal of impurities. The synthesis gas is then cooled further, and the excess process water is condensed and removed. The almost dry synthesis gas is then sent to the CO$_2$ removal section C, in which a larger or smaller part of the CO$_2$ is removed from the syngas.

The syngas, which now contains approximately no CO$_2$, is sent to the downstream FT synthesis section D as make-up gas, and the CO$_2$-rich stream obtained from the CO$_2$ removal process is either vented or kept for other use.

The process according to the invention offers a number of advantages over what was previously known. Thus, there is a reduced flow of inert compounds to the FT synthesis section, resulting in a more reactive gas as well as smaller equipment and piping with lower capital cost. Furthermore, no CO$_2$ recycle compressor is required, and this also reduces the capital cost.

The operation of the syngas unit is more stable without variations in the CO$_2$ recycle flow and composition.

The CO$_2$ removed from the syngas can be used for enhanced oil recovery (EOR).

In some cases the removal of CO$_2$ from the synthesis gas may also result in the need for higher tail gas recycle requirements, which may increase the efficiency.

In another embodiment of the invention, all the FT tail gas, which is not used for other purposes, such as fuel, is recycled. This is possible since the FT tail gas has a low impact on the syngas H$_2$/CO ratio on account of the low CO$_2$ content in the FT tail gas.

An advantage is that more FT tail gas can be recycled to the reformers and thereby a smaller part of the FT tail gas will be used as fuel and/or for power production. This means that the overall carbon efficiency of the plant from hydrocarbon feedstock (natural gas) to liquid hydrocarbon product (i.e. diesel and naphtha) is increased.

The syngas section can both be SMR and ATR or a combination of these reforming technologies. ATR reforming operates at lower S/C ratios than SMR reforming and produces a lower H$_2$/CO ratio and less CO$_2$ in the syngas. So CO$_2$ removal systems placed after an ATR are smaller than those placed after a SMR reformer. The syngas section will typically consist of one or more desulfurization reactors, an adiabatic pre-reformer and the main reformer (being either a SMR or ATR reformer). The FT tail gas can be routed through a pre-treatment reactor for conversion of olefin compounds. The pre-treatment reactor can be a dedicated reactor for olefin saturation (for example with a Cu-based catalyst), or it can be combined with the hydrogenation of organic sulfur compounds in the desulfurization reactors.

The addition point of the FT tail gas can be directly to the SMR or ATR reformer. Alternatively the FT tail gas can be added to the desulfurization reactors or to the adiabatic pre-reformer. Addition of the FT tail gas to a heat exchange reformer, if present, is also possible.

Fischer-Tropsch conditions are well-known to those skilled in the art. Preferably, the temperature is in the range of from 150 to 350° C., especially 180 to 240° C., and the pressure is in the range of from 100 to 10.000 kPa (0 to 100 barg), especially 1000 to 5000 kPa (10 to 50 barg). Any suitable Fischer-Tropsch catalyst may be used, but the most common are the transition metals cobalt, iron, and ruthenium. Nickel can also be used, but tends to favor methane formation ("methanation"). Cobalt-based catalysts are highly active, although iron may be more suitable for certain applications. Cobalt catalysts are more active for Fischer-Tropsch synthesis when the feed is natural gas. Natural gas has a high hydrogen-to-carbon ratio, so water gas shift (WGS) is not needed for cobalt catalysts. Iron catalysts are preferred for a lower quality feed such as coal or biomass. Synthesis gases derived from a hydrogen-poor feed have a low hydrogen content and require the WGS reaction.

The useful products obtained from the Fischer-Tropsch reactor will depend on the catalyst and the operating conditions used. In addition, the initial products may undergo further processing to obtain the desired products.

The invention also relates to a plant for carrying out the inventive process for the conversion of natural gas to hydrocarbon products.

Referring to FIG. 1, the plant according to the invention comprises a feed purification section (A), a syngas section (B), a $CO_2$ removal section (C) and a Fischer-Tropsch (FT) synthesis section (D).

The feed purification section (A) consists of one or several catalytic reactors, where impurities such as sulfur, chlorine and heavy metals are removed from the natural gas.

The syngas section (B) comprises one or several catalytic reactors and/or reformers, e.g. an adiabatic pre-reformer, a tubular reformer, a catalytic partial oxidation (CPO) reformer and/or an autothermal reformer (ATR). It may also include a heat exchange reformer, either in parallel with the SMR and/or ATR or upsteam and in series with the SMR and ATR. Furthermore, it may comprise a pre-reformer combined with an autothermal reformer (ATR).

The $CO_2$ removal in section (C) can be done by several techniques, including $CO_2$ wash systems and $CO_2$ membrane systems. Such systems are used in syngas plants for ammonia or CO plants for final clean-up of the syngas. The $CO_2$ removal section is normally seen as an extra capital investment, and it is not used in GTL plants based on Fischer-Tropsch synthesis.

The FT synthesis section (D) comprises one or more FT reactors, suitable examples of which include fixed bed reactors, such as tubular reactors, micro channel reactors and multiphase reactors with a stationary catalyst phase and slurry-bubble reactors. In a fixed bed reactor, the FT catalyst is held in a fixed bed contained in tubes or vessels within the reactor vessel. The syngas flowing through the reactor vessel contacts the FT catalyst contained in the fixed bed. The reaction heat is removed by passing a cooling medium around the tubes or vessels containing the fixed bed. For the slurry-bubble reactor, the FT catalyst particles are suspended in a liquid by the motion of bubbles of syngas sparged into the bottom of the reactor. As gas bubbles rise through the reactor, the syngas is absorbed in the liquid and diffuses to the catalyst for conversion to hydrocarbons. Gaseous products and unconverted syngas enter the gas bubbles and are collected at the top of the reactor. Liquid products are recovered from the suspending liquid using different techniques, such as separators, filtration, settling, hydrocyclones and magnetic techniques. Cooling coils immersed in the slurry remove heat generated by the reaction. Other possible embodiments of the FT reactor will be known by persons skilled in the art.

In the FT process, $H_2$ and CO combine via polymerization to form hydrocarbon compounds having various numbers of carbon atoms. Typically 70% conversion of syngas to FT liquids takes place in a single pass of the FT reactor unit. It is also common practice to arrange multiple FT reactors in series or parallel to achieve conversion levels of over 90%.

What is claimed is:

1. A process for the conversion of natural gas to hydrocarbon products, said process comprising the steps of:
    (a) mixing natural gas with hydrogen,
    (b) purifying the mixture from (a) in a feed purification section to obtain purified natural gas,
    (c) mixing the purified natural gas from (b) with steam to obtain a desired steam-to-carbon (S/C) ratio,
    (d) mixing the natural gas/steam mixture from (c) with all or a part of a tail gas from a downstream Fischer-Tropsch (FT) synthesis unit in a syngas section and converting the mixture into a synthesis gas,
    (e) cooling the synthesis gas from (d) and condensing out the process water from the synthesis gas from step (d),
    (f) leading the dry synthesis gas from (e) to a carbon dioxide removal section, where the $CO_2$ is removed from the synthesis gas, and
    (g) sending the $CO_2$-deprived synthesis gas to the downstream Fischer-Tropsch synthesis unit as a make-up gas,
    wherein the carbon dioxide removed from the syngas in step (f) is either vented or stored without any part of the $CO_2$ gas being recycled, and wherein no naphtha recycle is performed.

2. The process according to claim 1, wherein the feed purification section comprises one or more desulfurization reactors.

3. The process according to claim 1, wherein any non-recycled part of the tail gas from the FT synthesis unit is used as a fuel.

4. The process according to claim 1, wherein the syngas section consists of one or several catalytic reactors and/or reformers selected from the group consisting of an adiabatic pre-reformer, a tubular reformer and/or an autothermal reformer (ATR) consisting of a burner for partial oxidation of the feed stream with oxygen and an adiabatic catalyst bed.

5. The process according to claim 1, wherein the syngas section includes a heat exchange reformer, either in parallel with an SMR and/or ATR or upsteam and in series with the SMR and/or ATR.

6. The process according to claim 1, wherein the syngas section comprises a steam methane reformer (SMR), an autothermal reformer (AIR), a catalytic partial oxidation (CPO) reformer or a combination of these reforming technologies.

7. The process according to claim 1, wherein the syngas section comprises a pre-reformer combined with an autothermal reformer (ATR).

8. The process according to claim 1, wherein a part of the FT tail gas is added directly to an SMR, ATR or CPO reformer.

9. The process according to claim 1, wherein a part of the FT tail gas is added to desulfurization reactors or to an adiabatic pre-reformer.

10. The process according to claim 1, wherein a catalyst in the FT synthesis unit is based on a transition metal selected from the group consisting of cobalt, iron, and ruthenium.

* * * * *